United States Patent
Ookawa

(10) Patent No.: US 9,332,925 B2
(45) Date of Patent: May 10, 2016

(54) MAGNETIC RESONANCE IMAGING APPARATUS HAVING CONTINUOUS READOUT GRADIENT WITH GRADIENT SLEW RATE CHANGED

(75) Inventor: Masashi Ookawa, Otawara (JP)

(73) Assignee: TOSHIBA MEDICAL SYSTEMS CORPORATION, Otawara-Shi, Tochigi (JP)

( * ) Notice: Subject to any disclaimer, the term of this patent is extended or adjusted under 35 U.S.C. 154(b) by 626 days.

(21) Appl. No.: 13/154,839

(22) Filed: Jun. 7, 2011

(65) Prior Publication Data

US 2011/0298458 A1 Dec. 8, 2011

(30) Foreign Application Priority Data

Jun. 7, 2010 (JP) .................................. 2010-130271
Apr. 27, 2011 (JP) .................................. 2011-099935

(51) Int. Cl.
*A61B 5/05* (2006.01)
*G01R 33/54* (2006.01)
*A61B 5/055* (2006.01)

(52) U.S. Cl.
CPC ................ *A61B 5/055* (2013.01); *G01R 33/54* (2013.01); *G01R 33/546* (2013.01)

(58) Field of Classification Search
USPC ........................... 324/300–322; 600/407–435; 382/128–131
See application file for complete search history.

(56) References Cited

U.S. PATENT DOCUMENTS

| 4,689,563 A * | 8/1987 | Bottomley ......... G01R 33/3607 324/309 |
| 4,694,254 A * | 9/1987 | Vatis .................. G01R 33/3607 324/309 |
| 5,519,320 A | 5/1996 | Kanayama et al. |
| 5,757,187 A * | 5/1998 | Wollin .......................... 324/306 |
| 6,020,739 A * | 2/2000 | Meyer et al. ................... 324/309 |
| 6,031,746 A * | 2/2000 | Steigerwald et al. ........... 363/71 |
| 6,700,374 B1 * | 3/2004 | Wu .................... G01R 33/56554 324/309 |
| 7,039,455 B1 * | 5/2006 | Brosovich et al. ............. 600/509 |
| 7,737,690 B2 * | 6/2010 | Xu et al. ........................ 324/307 |
| 7,853,318 B2 * | 12/2010 | Wedan .......................... 600/509 |
| 8,115,563 B2 * | 2/2012 | Odagiri ......................... 332/109 |
| 8,941,381 B2 * | 1/2015 | Feinberg et al. .............. 324/309 |
| 2008/0068014 A1 * | 3/2008 | Dannels ............... G01R 33/561 324/312 |

(Continued)

FOREIGN PATENT DOCUMENTS

CN 1247319 A 3/2000
JP H05-031096 2/1993

(Continued)

OTHER PUBLICATIONS

Office Action dated Jun. 13, 2014 in CN 201110156434.7.

(Continued)

*Primary Examiner* — Melissa Koval
*Assistant Examiner* — Tiffany Fetzner
(74) *Attorney, Agent, or Firm* — Nixon & Vanderhye P.C.

(57) ABSTRACT

A magnetic resonance imaging apparatus according to an embodiment includes a sequence control unit that controls a gradient magnetic field power supply, thereby performing a pulse sequence including the application of a continuous readout gradient magnetic field pulse. The sequence control unit controls the gradient magnetic field power supply such that the slew rate of the gradient magnetic field pulse is reduced in stages as the output voltage of a gradient magnetic field amplifier is reduced in stages.

15 Claims, 8 Drawing Sheets

(56) References Cited

U.S. PATENT DOCUMENTS

| | | | |
|---|---|---|---|
| 2008/0228092 A1* | 9/2008 | Wedan | 600/509 |
| 2008/0284439 A1* | 11/2008 | Xu et al. | 324/322 |
| 2010/0321570 A1* | 12/2010 | Odagiri | 348/500 |
| 2011/0089942 A1* | 4/2011 | Goodwill et al. | 324/301 |
| 2011/0298458 A1* | 12/2011 | Ookawa | 324/309 |
| 2012/0056620 A1* | 3/2012 | Feinberg et al. | 324/309 |
| 2012/0105155 A1* | 5/2012 | Odagiri | 330/207 A |
| 2012/0165904 A1* | 6/2012 | Lee et al. | 607/90 |
| 2013/0289386 A1* | 10/2013 | Deisseroth et al. | 600/411 |

FOREIGN PATENT DOCUMENTS

| | | |
|---|---|---|
| JP | H05-277085 | 10/1993 |
| JP | H08-024236 A | 1/1996 |
| JP | 8-056917 | 3/1996 |
| JP | 9-248285 | 9/1997 |

OTHER PUBLICATIONS

English translation of Office Action mailed Dec. 16, 2014 in JP 2011-099935.

* cited by examiner

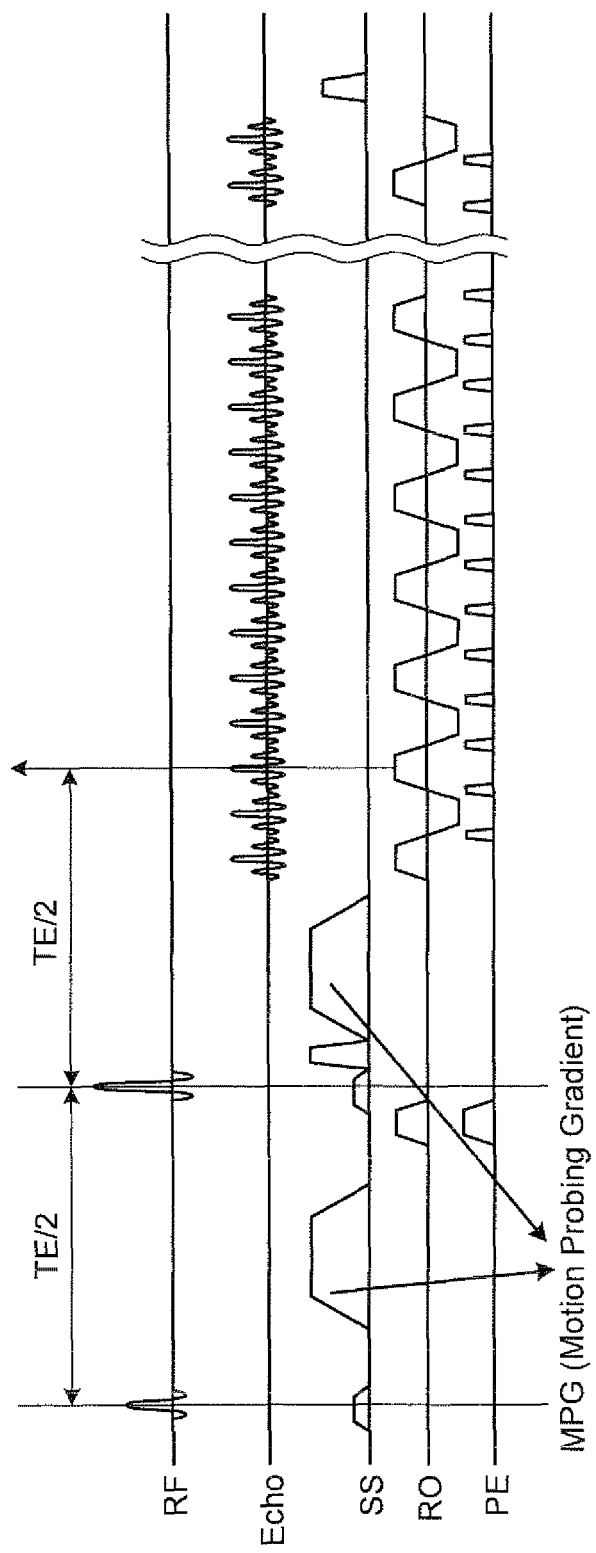

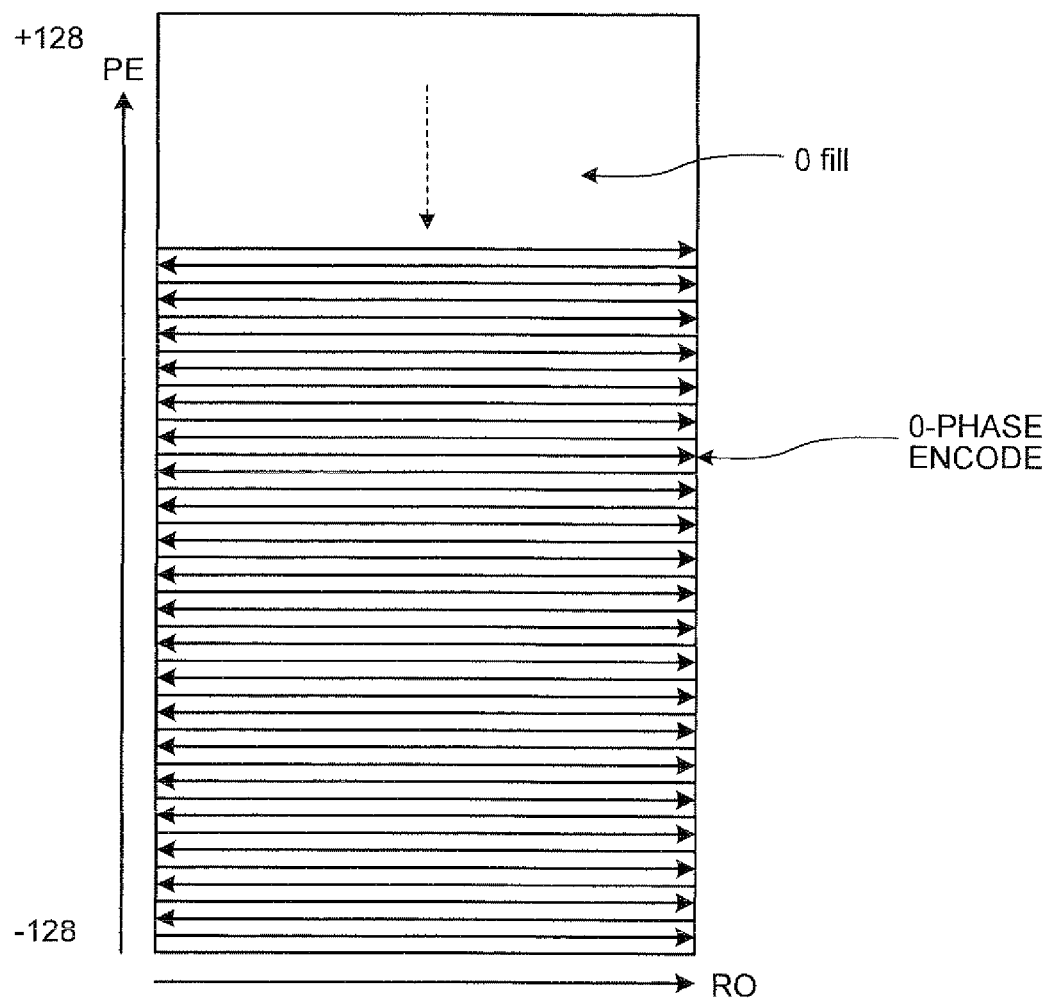

MAGNETIC RESONANCE IMAGING APPARATUS HAVING CONTINUOUS READOUT GRADIENT WITH GRADIENT SLEW RATE CHANGED

CROSS-REFERENCE TO RELATED APPLICATIONS

This application is based upon and claims the benefit of priority from Japanese Patent Application No. 2010-130271, filed on Jun. 7, 2010; and Japanese Patent Application No. 2011-99935, filed on Apr. 27, 2011, the entire contents of all of which are incorporated herein by reference.

FIELD

Embodiments described herein relate generally to a magnetic resonance imaging apparatus.

BACKGROUND

As one of the imaging methods using a magnetic resonance imaging apparatus (hereinafter, an MRI apparatus), for example, there is a pulse sequence including the application of a continuous readout gradient magnetic field pulse, such as an echo planar imaging (EPI) sequence. The MRI apparatus includes a gradient magnetic field amplifier that amplifies a current to be supplied to a gradient coil. When the pulse sequence is performed, the output voltage of the gradient magnetic field amplifier is likely to be reduced in stages since a large load is applied to the gradient magnetic field amplifier. When the output voltage of the gradient magnetic field amplifier is reduced, it is difficult to maintain a variation in the gradient magnetic field per unit time (hereinafter, referred to as a slew rate (SR)) and thus maintain the waveform of the gradient magnetic field pulse.

Therefore, in the related art, imaging conditions are designed in accordance with the minimum output voltage of the gradient magnetic field amplifier, that is, the minimum slew rate.

However, in the related art, the flexibility of the imaging conditions is reduced. In addition, there is a concern that resolution will not be improved, an echo train spacing (ETS) will be extended, and the number of echoes will be restricted. Therefore, it is necessary to improve the flexibility of the imaging conditions.

BRIEF DESCRIPTION OF THE DRAWINGS

FIG. 8 is a diagram of an EPI sequence according to a third embodiment;
and
FIG. 9 is a diagram of a collected MR echo signal.

DETAILED DESCRIPTION

The magnetic resonance imaging apparatus according the present embodiments includes a sequence control unit. The sequence control unit controls a gradient magnetic field power supply, thereby performing a pulse sequence including the application of a continuous readout gradient magnetic field pulse, wherein the sequence control unit controls the gradient magnetic field power supply such that a slew rate of the gradient magnetic field pulse is reduced in stages as an output voltage of a gradient magnetic field amplifier is reduced in stages.

Hereinafter, as an example of an MRI apparatus according to embodiments, MRI apparatuses 100 according to first and second embodiments will be described.

First, the structure of the MRI apparatus 100 according to the first embodiment will be described with reference to FIG. 1.

Figure 1:
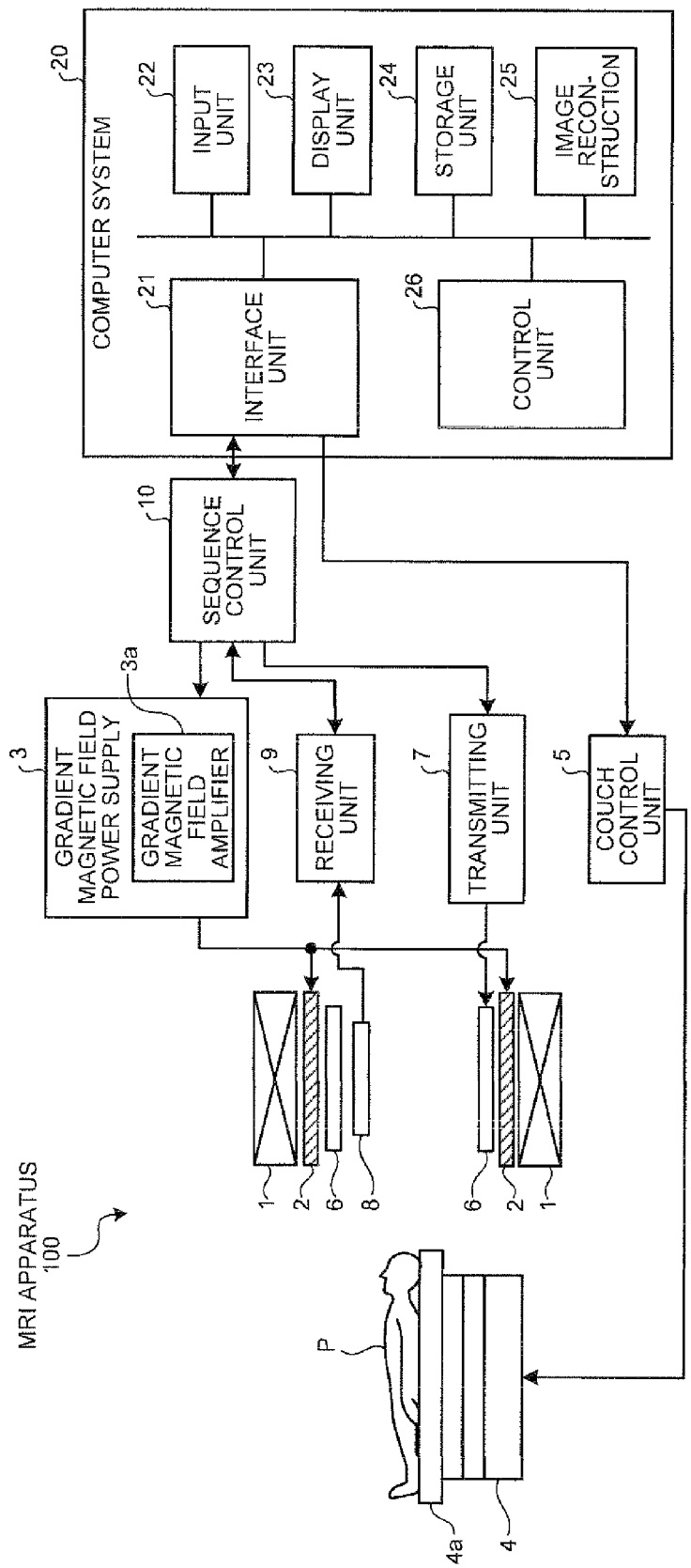
FIG. 1 is a diagram of the structure of an MRI apparatus according to a first embodiment.

FIG. 1 is a diagram illustrating the structure of the MRI apparatus 100 according to the first embodiment. As shown in FIG. 1, the MRI apparatus 100 according to the first embodiment includes a static magnetic field magnet 1, a gradient coil 2, a gradient magnetic field power supply 3, a couch 4, a couch control unit 5, a transmitting coil 6, a transmitting unit 7, a receiving coil 8, a receiving unit 9, a sequence control unit 10, and a computer system 20.

The static magnetic field magnet 1 is formed in a hollow cylindrical shape and generates a uniform static magnetic field therein. For example, a permanent magnet or a superconductive magnet is used as the static magnetic field magnet 1. The gradient coil 2 is formed in a hollow cylindrical shape and generates a gradient magnetic field therein. Specifically, the gradient coil 2 is provided in the static magnetic field magnet 1, is supplied with a current from the gradient magnetic field power supply 3, and generates a gradient magnetic field.

The gradient magnetic field power supply 3 supplies a current to the gradient coil 2 according to pulse sequence execution data (also referred to as an instruction signal) transmitted from the sequence control unit 10. As shown in FIG. 1, the gradient magnetic field power supply 3 includes a gradient magnetic field amplifier 3a. The gradient magnetic field amplifier 3a amplifies the current to be supplied to the gradient coil 2.

The couch 4 includes a top plate 4a on which an examinee P lies and the top plate 4a on which the examinee P lies is inserted into a hollow tube (imaging hole) of the gradient coil 2. In general, the couch 4 is provided such that the longitudinal direction thereof is parallel to the central axis of the static magnetic field magnet 1. The couch control unit 5 drives the couch 4 such that the top plate 4a is moved in the horizontal and vertical directions.

The transmitting coil 6 generates a radio frequency (RF) magnetic field. Specifically, the transmitting coil 6 is provided in the gradient coil 2, is supplied with an RF pulse from the transmitting unit 7, and generates an RF magnetic field. The transmitting unit 7 applies an RF pulse corresponding to a resonance frequency (Larmor frequency) to the transmitting coil 6 according to the pulse sequence execution data transmitted from the sequence control unit 10.

The receiving coil 8 receives an MR echo signal. Specifically, the receiving coil 8 is provided in the gradient coil 2 and receives the MR echo signal emitted from the examinee P by the influence of the high-frequency magnetic field. When receiving the MR echo signal, the receiving coil 8 outputs the MR echo signal to the receiving unit 9. For example, the receiving coil 8 is a receiving coil for the head, a receiving coil for the spine, a receiving coil for the abdomen, or the like.

The receiving unit 9 generates MR echo signal data on the basis of the MR echo signal output from the receiving coil 8 according to the pulse sequence execution data transmitted from the sequence control unit 10. Specifically, the receiving unit 9 converts the MR echo signal output from the receiving coil 8 into a digital signal, thereby generating MR echo signal data. Then, the receiving unit 9 transmits the generated MR echo signal data to the computer system 20 through the sequence control unit 10. In addition, the receiving unit 9 may be provided in a gantry including, for example, the static magnetic field magnet 1 and the gradient coil 2.

The sequence control unit 10 controls the gradient magnetic field power supply 3, the transmitting unit 7, and the receiving unit 9. Specifically, the sequence control unit 10 transmits the pulse sequence execution data transmitted from the computer system 20 to the gradient magnetic field power supply 3, the transmitting unit 7, and the receiving unit 9, thereby controlling the gradient magnetic field power supply 3, the transmitting unit 7, and the receiving unit 9.

The computer system 20 includes an interface unit 21, an input unit 22, a display unit 23, a storage unit 24, an image reconstruction unit 25, and a control unit 26. The interface unit 21 is connected to the sequence control unit 10 and controls the input and output of data between the sequence control unit 10 and the computer system 20.

The input unit 22 receives, for example, imaging conditions input by the operator. For example, the input unit 22 is a pointing device, such as a mouse or a trackball, a selection device, such as a mode switch, or an input device, such as a keyboard. The display unit 23 displays, for example, a graphical user interface (GUI) for inputting the imaging conditions or a reconstructed MR image. For example, the display unit 23 is a display device, such as a liquid crystal display.

The storage unit 24 stores, for example, MR images or data used in the MRI apparatus 100. For example, the storage unit 24 is a semiconductor memory device, such as a random access memory (RAM) or a flash memory, a hard disk, or an optical disk.

The image reconstruction unit 25 reconstructs an MR image. Specifically, the image reconstruction unit 25 arranges the MRI echo signal data transmitted from the receiving unit 9 in the k-space and performs Fourier transform to reconstruct an MR image.

The control unit 26 controls each of the above-mentioned units to control the overall operation of the MRI apparatus 100. For example, the control unit 26 is an integrated circuit, such as an application specific integrated circuit (ASIC) or a field programmable gate array (FPGA), or an electronic circuit, such as a central processing unit (CPU) or a micro processing unit (MPU).

In the above-mentioned structure, for example, when an EPI sequence is performed, the MRI apparatus 100 according to the first embodiment performs control such that the slew rate of a gradient magnetic field pulse is reduced in stages as the output voltage of the gradient magnetic field amplifier 3a is reduced in stages. Next, the control operation will be described.

Figure 2:
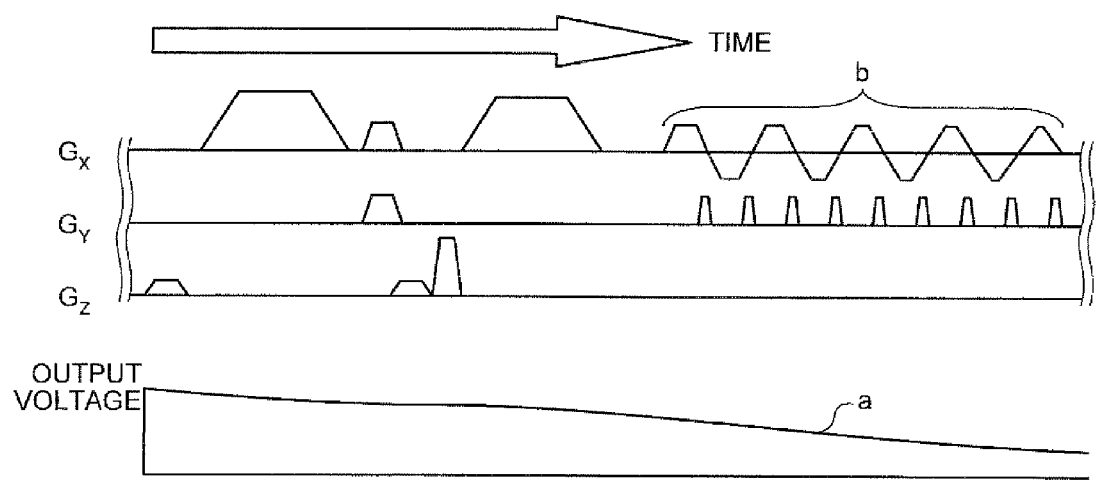
FIG. 2 is a diagram of an EPI sequence.

FIG. 2 is a diagram illustrating the EPI sequence. The sequence control unit 10 according to the first embodiment performs the EPI sequence shown in FIG. 2. In FIG. 2, "$G_X$," "$G_Y$," and "$G_Z$" correspond to an "X-axis gradient magnetic field power supply $3_X$," a "Y-axis gradient magnetic field power supply $3_Y$," and a "Z-axis gradient magnetic field power supply $3_Z$" of the gradient magnetic field power supply 3, respectively. In FIG. 2, an output voltage a indicates the output voltage of the gradient magnetic field amplifier 3a. As those in the art will appreciate, in this exemplary depiction of a one-shot EPI sequence, each $G_X$ pulse is applied during readout of echo data that is collected and stored at one line location in k-space, the line being located in k-space according to respectively corresponding phase-encoding of the collected data effected by phase-encoding $G_Y$ pulses applied between successive $G_X$ data collection periods during readout sequence period b.

As shown in FIG. 2, the EPI sequence includes the application of a continuous readout gradient magnetic field pulse (see reference numeral b) within one shot. The application of the continuous readout gradient magnetic field pulse involves high-speed switching and the wave height value of the readout gradient magnetic field pulse is not small. In the pulse sequence, since a large load is applied to the gradient magnetic field amplifier 3a, the output voltage a of the gradient magnetic field amplifier 3a is likely to be reduced in stages, as shown in FIG. 2.

Therefore, the sequence control unit 10 according to the first embodiment controls the gradient magnetic field power supply 3 such that the slew rate (a variation in the gradient magnetic field per unit time) of the gradient magnetic field pulse is reduced in stages as the output voltage of the gradient magnetic field amplifier 3a is reduced in stages. As can be seen from FIG. 2, in the EPI sequence performed by the sequence control unit 10, the slew rate of the waveform of the gradient magnetic field pulse (reference numeral b) that is applied with a continuous period is reduced in stages. For convenience of explanation, in FIG. 2, a variation in the waveform is emphasized.

Figure 3:
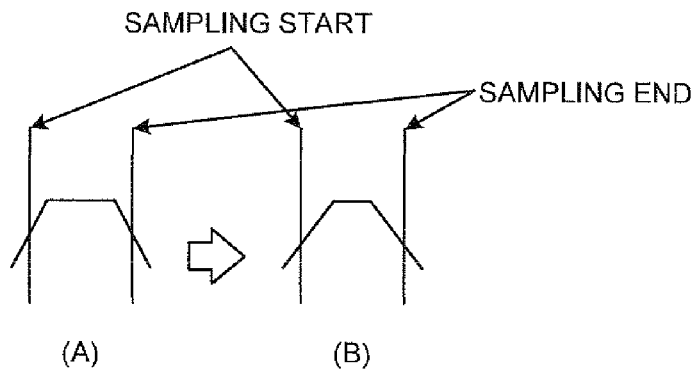
FIG. 3 is a diagram of a reduction in the slew rate.

FIG. 3 is a diagram illustrating a reduction in the slew rate. (A) and (B) of FIG. 3 show aspects in which the slew rate of the gradient magnetic field pulse is reduced. That is, the comparison between the waveform of the gradient magnetic field pulse shown in (A) of FIG. 3 and the waveform of the gradient magnetic field pulse shown in (B) of FIG. 3 show that the rising gradient of the waveform of the gradient magnetic field pulse shown in (B) of FIG. 3 is less than that of the waveform of the gradient magnetic field pulse shown in (A) of FIG. 3.

In addition, as shown in FIG. 2, the sequence control unit 10 according to the first embodiment controls the gradient magnetic field power supply 3 such that the rising gradient is gradually reduced whenever a read-out operation is performed. In the first embodiment, a method of reducing the rising gradient whenever the read-out operation is performed is used, but the embodiment is not limited thereto. For example, a method of reducing the rising gradient whenever a plurality of read-out operations is performed may be used. For example, the continuous readout gradient magnetic field pulses may be classified into, for example, three groups and a slew rate that is gradually reduced may be allocated to each group.

As can be seen from "sampling start" and "sampling end" shown in FIG. 3, it is assumed that the sequence control unit 10 according to the first embodiment collects MR echo signals using RAMP sampling. There is a method of starting sampling after the rising of the gradient magnetic field pulse. A RAMP sampling method starts sampling without waiting for the rising of the gradient magnetic field pulse. The ratio of the MR echo signal collected during rising and the MR echo signal collected after rising is a variable RAMP sampling rate.

In the EPI sequence shown in FIG. 2, the rising gradient of the gradient magnetic field pulse is gradually reduced. Therefore, when the RAMP sampling is not used, it is considered that the sampling time is variable. However, when the RAMP sampling is used, the sampling time is constant. The embodiment is not limited to the RAMP sampling. A method of starting sampling after the rising of the gradient magnetic field pulse may be used.

Figure 4A:
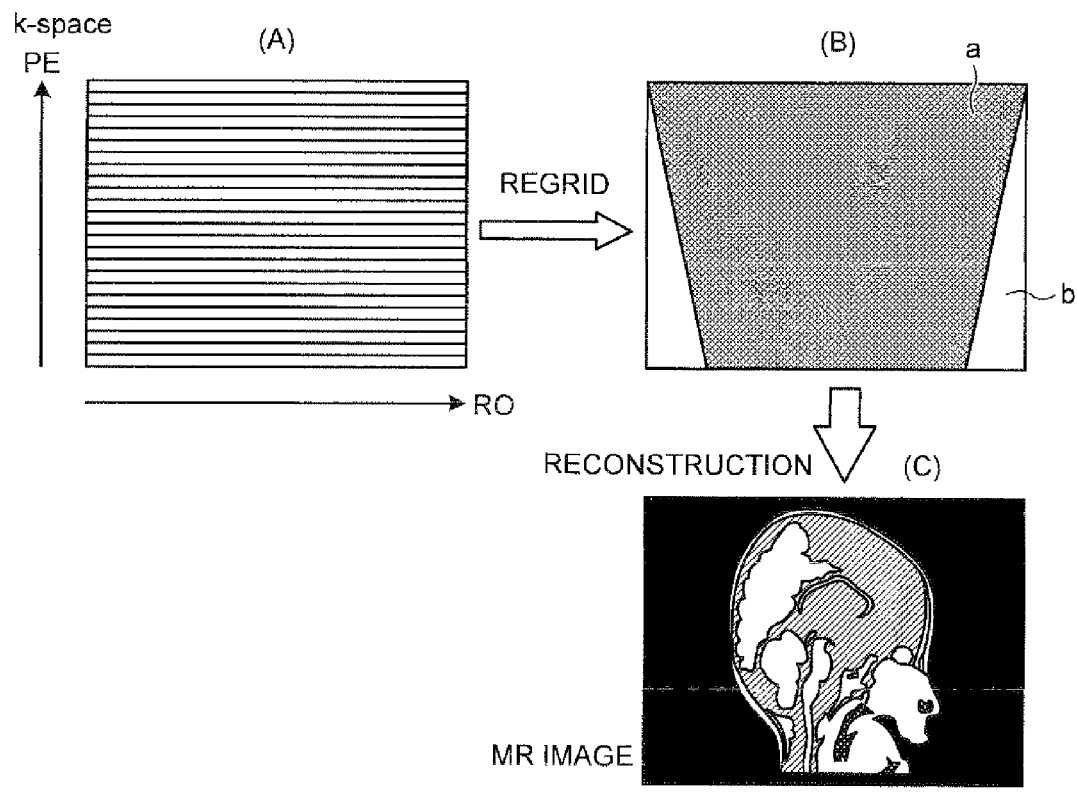
FIG. 4A is a diagram of the relationship between a collected MR echo signal and a reconstructed MR image.

Next, the relationship between the collected MR echo signal and the reconstructed MR image will be described. FIG. 4A is a diagram illustrating the relationship between the collected MR echo signal and the reconstructed MR image. As shown in (A) of FIG. 4A, the MR echo signal data generated by the receiving unit 9 is arranged at different locations in the k-space by the image reconstruction unit 25 of the computer system 20. In addition, as shown in (B) of FIG. 4A, the image reconstruction unit 25 performs regridding on the MR echo signal data arranged at different locations in the k-space.

As can be seen from the comparison between (A) and (B) of FIG. 3, the numbers of sampling points are equal to each other in the gradient magnetic field pulses. However, since the rising gradients of the gradient magnetic field pulses are different from each other, the areas of the gradient magnetic fields are different from each other. The difference between the areas means that valid data obtained by regridding is different. Returning to FIG. 4A, as can be seen from the regridded (B), the region a of valid data is gradually reduced and the region b of invalid data gradually increases from the upper side to the lower side. The time axis direction of the MR echo signal data collected by the EPI sequence extends from the upper side to the lower side in (B) of FIG. 4A.

As such, in the EPI sequence according to the first embodiment, the rising gradient of the gradient magnetic field pulse is gradually reduced. As a result, as shown in (3) of FIG. 4A, the valid data is gradually reduced, but is more than the valid data in the pulse sequence when the imaging conditions are designed in accordance with the minimum slew rate, which contributes to improving the quality of the MR image. (C) of FIG. 4A shows an example of the reconstructed MR image.

Figure 4B:
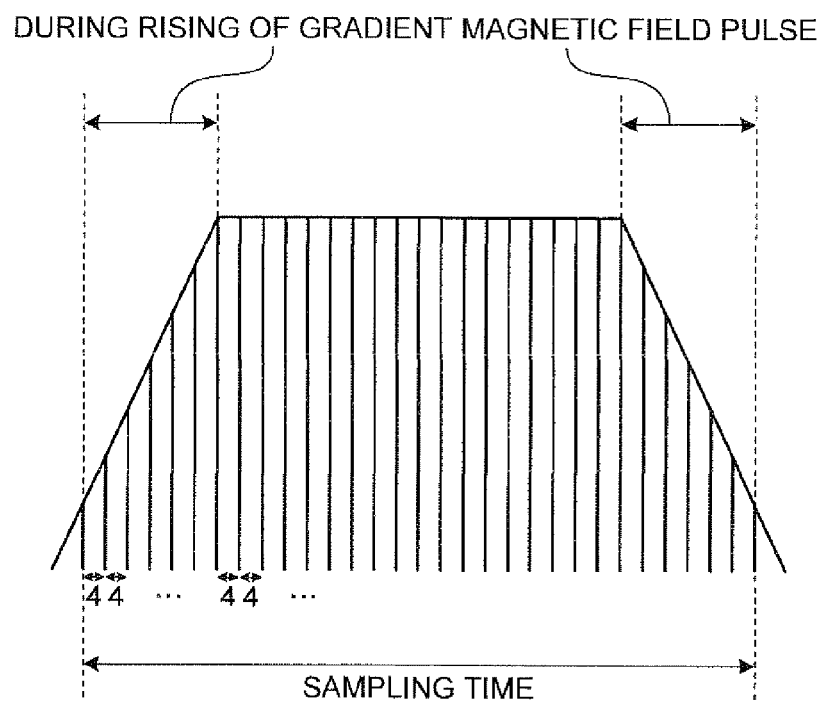
FIG. 4B is a diagram of the collection of the MR echo signal by RAMP sampling.
Figure 4C:
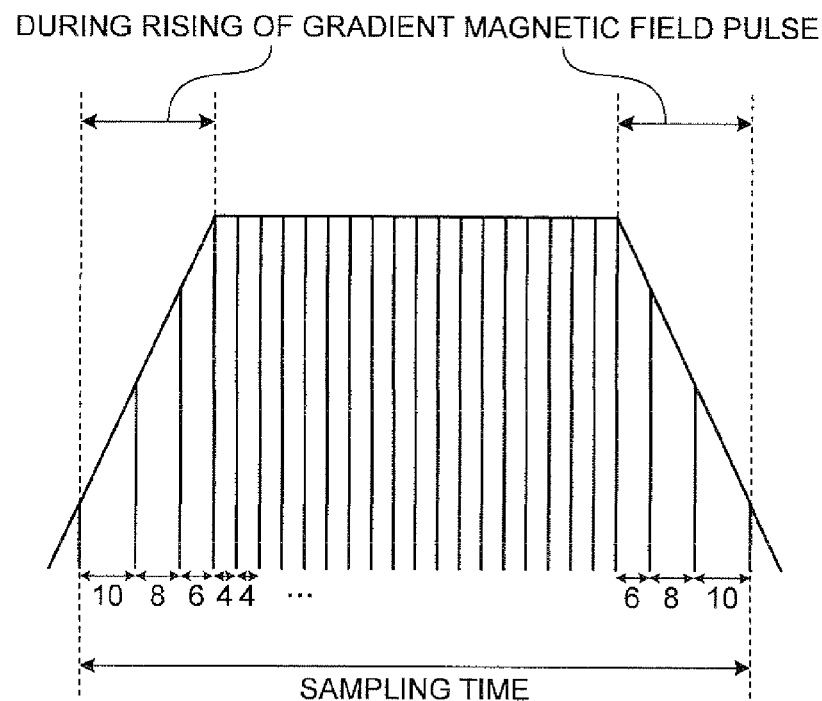
FIG. 4C is a diagram of the collection of the MR echo signal by RAMP sampling.

Next, the collection of the MR echo signal by the RAMP sampling will be described in detail with reference to FIGS. 4B and 4C. FIGS. 4B and 4C are diagrams illustrating the collection of the MR echo signal data to be stored at respective locations in k-space by the RAMP sampling.

As described above, the RAMP sampling is a method of starting sampling without waiting for the rising of the gradient magnetic field pulse. The RAMP sampling is divided into the following two methods: a method (hereinafter, referred to as a fixed pitch method) of fixing a sampling pitch using an analog digital converter (ADC), as shown in FIG. 4B; and a method (hereinafter, referred to as a variable pitch method) of changing a sampling pitch, as shown in FIG. 4C.

First, in the fixed pitch method, the pitch is constant during sampling, as shown in FIG. 4B. In the example shown in FIG. 4B, the pitch is, for example, "4." In FIG. 3, the numbers of sampling points are equal to each other in (A) and (B) of FIG. 3, which corresponds to the fixed pitch method. That is, in the fixed pitch method, during the rising of the gradient magnetic field pulse, the area of the gradient magnetic field pulse varies, for example, during each sampling time. Therefore, regridding is needed.

In this case, the image reconstruction unit 25 that reconstructs images needs to change a coefficient for regridding when the slew rate of the gradient magnetic field pulse is reduced in stages. Therefore, (the pulse sequence execution data is generated in advance by the control unit 26 of the computer system 20, which will be described below) for example, the control unit 26 calculates the coefficient for regridding from the pulse sequence execution data that has been generated and notifies the calculated coefficient to the image reconstruction unit 25 in advance. Then, the image reconstruction unit 25 performs regridding on the MR echo signal data arranged in the k-space using the coefficient notified by the control unit 26.

In the variable pitch method, as shown in FIG. 4C, the pitch is constant after the rising of the gradient magnetic field pulse, but is variable during the rising of the gradient magnetic field pulse. In the example shown in FIG. 4C, the pitch has a variable value of, for example, "10," "8," and "6." In this case, the number of sampling points is reduced in stages as the slew rate of the gradient magnetic field pulse is reduced in stages. That is, in the variable pitch method, the pitch is adjusted such that the area of the gradient magnetic field pulse is constant. Therefore, the number of sampling points is reduced. In the variable pitch method, the amount of collected data is reduced, but a reduction in the region of the valid data shown in (B) of FIG. 4A does not occur. The regridding operation of the image reconstruction unit 25 is not needed.

In this case, the receiving unit 9 that receives MR echo signals needs to change the pitch of the ADC when the slew rate of the gradient magnetic field pulse is reduced in stages. Therefore, for example, the control unit 26 calculates an appropriate pitch from the generated pulse sequence execution data and notifies the calculated pitch to the receiving unit 9 through the sequence control unit 10. Then, the receiving unit 9 converts the MR echo signal into a digital signal using the notified pitch.

In this embodiment, the control unit 26 calculates the coefficient for regridding or the pitch, but the embodiment is not limited thereto. For example, the image reconstruction unit 25 or the receiving unit 9 may calculate the coefficient or the pitch. This is, the calculation structure may be appropriately changed depending on the operation conditions.

The EPI sequence performed by the sequence control unit 10 according to the first embodiment has been described above. In the first embodiment, the pulse sequence execution data for performing the EPI sequence is generated by the control unit 26 of the computer system 20 in advance.

Figure 5:
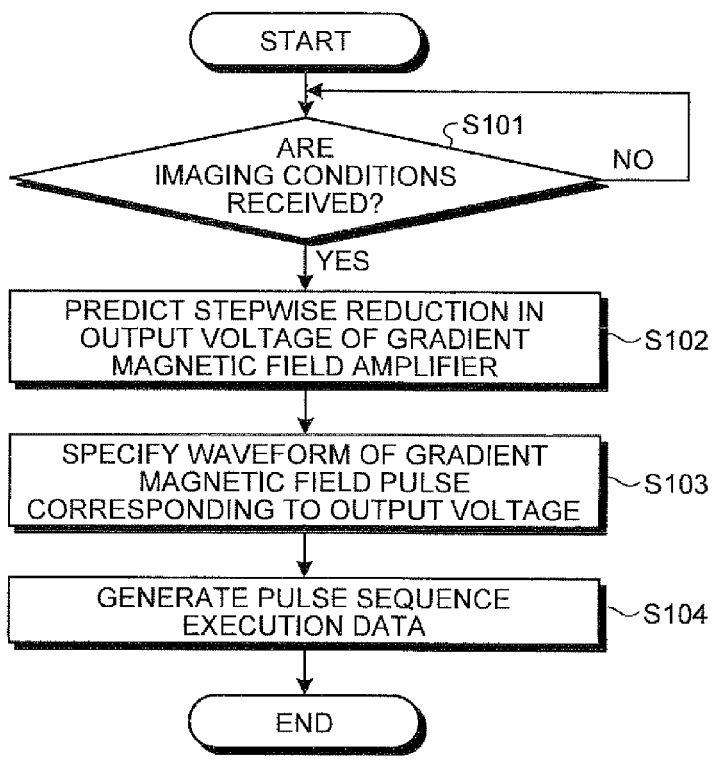
FIG. 5 is a flowchart of the procedure of a pulse sequence execution data generating process according to the first embodiment.

FIG. 5 is a flowchart illustrating the procedure of a pulse sequence execution data generating process according to the first embodiment. As shown in FIG. 5, the control unit 26 determines whether the imaging conditions input by the operator of the MRI apparatus 100 are received (Step S101). When it is determined that the imaging conditions are received (Step S101: Yes), the control unit 26 predicts a stepwise reduction in the output voltage of the gradient magnetic field amplifier 3a on the basis of the received imaging conditions (Step S102).

For example, the computer system 20 acquires information indicating the correlation between the imaging conditions and the downward tendency of the output voltage (variation in the output voltage) by experiments or measurement in advance and stores the acquired information in the storage unit 24. Then, the control unit 26 acquires the downward tendency of the output voltage that is stored so as to be associated with the imaging conditions using the received imaging conditions with reference to the information stored in the storage unit 24. Then, the control unit 26 uses the acquired downward tendency as the prediction result.

Then, the control unit 26 specifies the waveform of the gradient magnetic field pulse corresponding to the output voltage (Step S103). For example, the control unit 26 calculates a rising gradient corresponding to the downward tendency predicted in Step S102 using a predetermined expression and associates the output voltage with the calculated rising gradient to specify the waveform of the gradient magnetic field pulse corresponding to the output voltage. Since the output voltage is reduced in stages, a plurality of waveforms of the gradient magnetic field pulse is specified in accordance with the stepwise reduction.

The control unit 26 generates pulse sequence execution data such that the waveform of the gradient magnetic field pulse specified in Step S103 is reflected (Step S104). Then, the sequence control unit 10 executes the generated pulse sequence execution data to perform the EPI sequence shown in FIG. 2.

As described above, the MRI apparatus 100 according to the first embodiment includes the sequence control unit 10 that controls the gradient magnetic field power supply 3 using the pulse sequence execution data, thereby performing the pulse sequence including the application of a continuous readout gradient magnetic field pulse. The sequence control unit 10 controls the gradient magnetic field power supply 3 such that the slew rate of the gradient magnetic field pulse is reduced in stages as the output voltage of the gradient magnetic field amplifier 3a is reduced in stages. As those in the art will appreciate, this means that the slew rate of the waveform is changed according to the location in k-space of MR echo signal data to be collected.

Specifically, in the MRI apparatus 100 according to the first embodiment, when receiving the imaging conditions, the control unit 26 predicts a stepwise reduction in the output voltage on the basis of the received imaging conditions, specifies the waveform of the gradient magnetic field pulse corresponding to the predicted stepwise reduction, and generates pulse sequence execution data on the basis of the specification result. The sequence control unit 10 controls the gradient magnetic field power supply 3 using the generated pulse sequence execution data.

In this way, according to the first embodiment, it is possible to improve the flexibility of the imaging conditions. In addition, for example, it is possible to improve resolution, prevent the extension of ETS to reduce distortion (magnetic susceptibility artifact), and prevent restrictions in the number of echoes.

Next, a second embodiment will be described. In the first embodiment, the pulse sequence execution data for performing the EPI sequence is generated in advance by the control unit 26 of the computer system 20 and the generated pulse sequence execution data is used to control the gradient magnetic field power supply 3 without any change. In contrast, in the second embodiment, the pulse sequence execution data for performing the EPI sequence is dynamically changed during an imaging operation.

Figure 6:
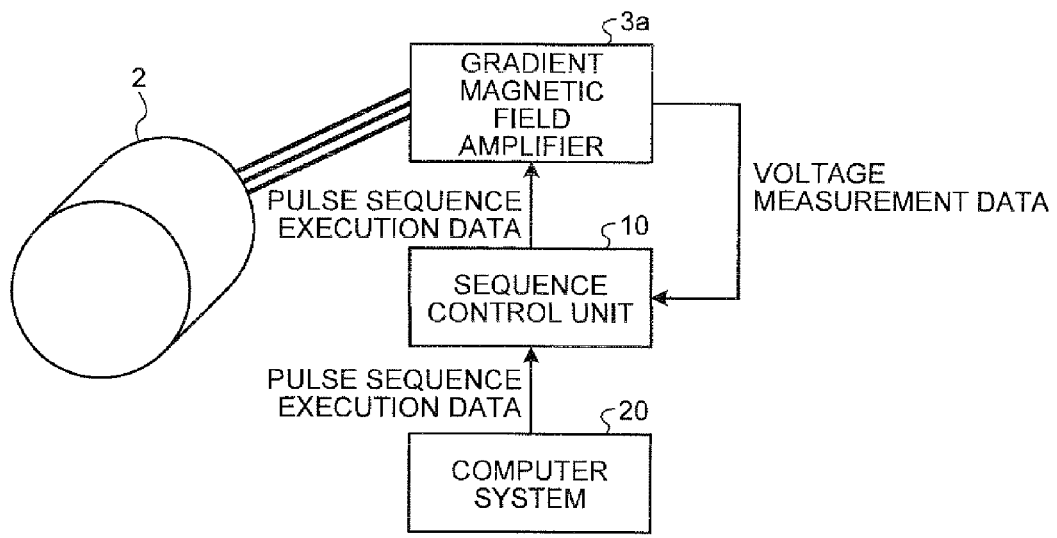
FIG. 6 is a diagram of the outline of a change in pulse sequence execution data according to a second embodiment.

FIG. 6 is a diagram illustrating the outline of a change in the pulse sequence execution data according to the second embodiment. As shown in FIG. 6, a gradient magnetic field amplifier 3a according to the second embodiment measures the output voltage using monitoring and feeds back voltage measurement data to the sequence control unit 10.

The sequence control unit 10 transmits the pulse sequence execution data transmitted from the computer system 20 to the gradient magnetic field power supply 3, thereby controlling the gradient magnetic field power supply 3. When receiving the voltage measurement data that is fed back, the sequence control unit 10 according to the second embodiment calculates a rising gradient corresponding to the output voltage which is indicated by the received voltage measurement data and changes a corresponding portion of the pulse sequence execution data according to the calculation result. Then, the sequence control unit 10 transmits the changed pulse sequence execution data to the gradient magnetic field power supply 3.

Figure 7:
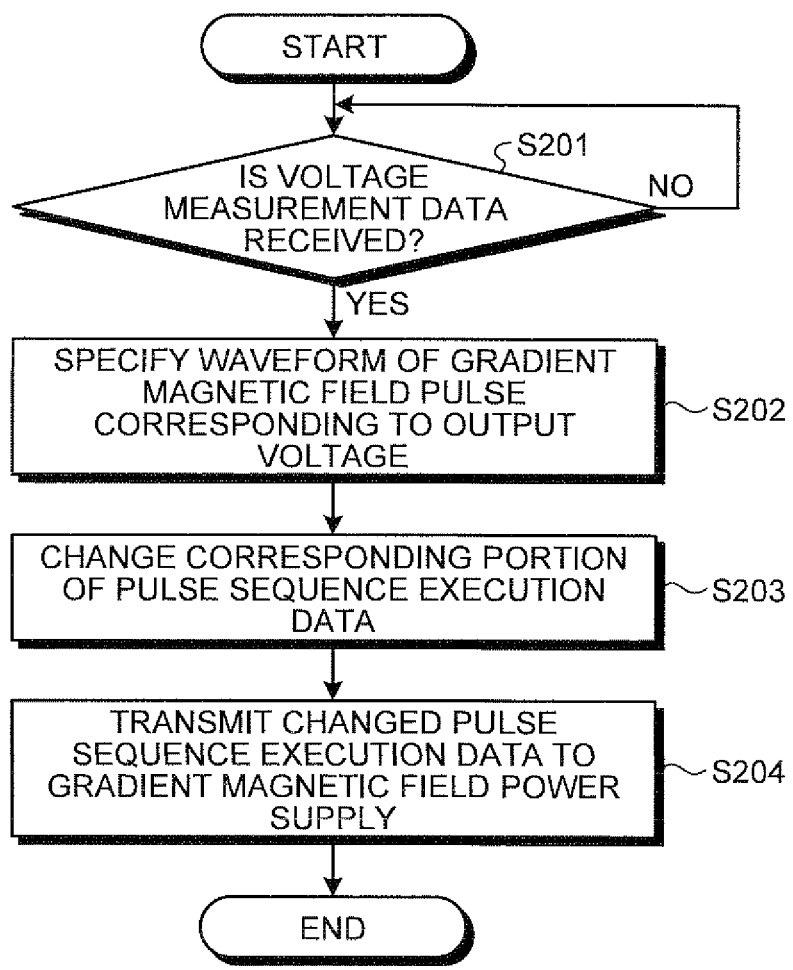
FIG. 7 is a flowchart of the procedure of a pulse sequence execution data change process according to a second embodiment.

FIG. 7 is a flowchart illustrating the procedure of a pulse sequence execution data change process according to the second embodiment. As shown in FIG. 7, the sequence control unit 10 determines whether the voltage measurement data is received from the gradient magnetic field amplifier 3a (Step S201). When it is determined that the voltage measurement data is received (Step S201: Yes), the sequence control unit 10 specifies the waveform of the gradient magnetic field pulse corresponding to the output voltage on the basis of the received voltage measurement data (Step S202).

Then, the sequence control unit 10 changes a corresponding portion of the pulse sequence execution data transmitted from the computer system 20 (Step S203) and transmits the changed pulse sequence execution data to the gradient magnetic field power supply 3 (Step S204).

In the second embodiment, since the waveform of the gradient magnetic field pulse corresponding to the output voltage is specified on the basis of the voltage measurement data that is fed back, only a portion of the pulse sequence execution data, that is, a portion of the pulse sequence execution data corresponding to the actual execution timing is changed. In other words, the sequence control unit 10 receives a series of pulse sequence execution data from the computer system 20. Only a portion of the changed pulse sequence execution data which corresponds to the actual execution timing is transmitted from the sequence control unit 10 to the gradient magnetic field power supply 3. The sequence control unit 10 according to the second embodiment repeatedly performs Steps S201 to S204.

As described in the first embodiment, during the collection of the MR echo signal by RAMP sampling, the regridding coefficient needs to be changed with a stepwise reduction in the slew rate of the gradient magnetic field pulse in the fixed pitch method, and the pitch needs to be changed with a stepwise reduction in the slew rate of the gradient magnetic field pulse in the variable pitch method. Once again, as will be appreciated by those in the art, a waveform is specified having a slew rate that is changed according to a location in k-space of MR echo signal data to be collected.

As in the second embodiment, when the sequence control unit 10 changes a corresponding portion of the pulse sequence execution data on the basis of the voltage measurement data that is fed back, for example, the sequence control unit 10 may notify the information of the changed pulse sequence execution data to the control unit 26, and the control unit 26 may calculate a coefficient for regridding on the basis of the notified information and transmit the calculated coefficient to the image reconstruction unit 25.

For example, the sequence control unit 10 may calculate the pitch and notify the calculated pitch to the receiving unit 9.

In this embodiment, the control unit 26 or the sequence control unit 10 calculates the coefficient for regridding or the pitch, but the embodiment is not limited thereto. For example, the image reconstruction unit 25 or the receiving unit 9 may calculate the coefficient for regridding or the pitch. The calculation structure may be appropriately changed depending on the operation conditions.

As described above, the MRI apparatus 100 according to the second embodiment includes the sequence control unit 10 that controls the gradient magnetic field power supply 3 on the basis of the pulse sequence execution data, thereby performing the pulse sequence including the application of a continuous readout gradient magnetic field pulse. The sequence control unit 10 controls the gradient magnetic field power supply such that the slew rate of the gradient magnetic field pulse is reduced in stages as the output voltage of the gradient magnetic field amplifier 3a is reduced in stages.

Specifically, in the MRI apparatus 100 according to the second embodiment, the gradient magnetic field power supply 3 measures the output voltage of the gradient magnetic field amplifier 3a using monitoring and feeds back the measurement result to the sequence control unit 10. Then, when receiving the measured output voltage, the sequence control unit 10 specifies the waveform of the gradient magnetic field pulse corresponding to the output voltage, changes the pulse sequence execution data on the basis of the specification result, and controls the gradient magnetic field power supply 3 using the changed pulse sequence execution data.

In this way, according to the second embodiment, similarly to the first embodiment, it is possible to improve the flexibility of the imaging conditions. In addition, similarly to the first embodiment, it is possible to improve resolution, prevent the extension of ETS to reduce distortion (magnetic susceptibility artifact), and prevent restrictions in the number of echoes.

Further, according to the second embodiment, the gradient magnetic field amplifier 3a with various output voltage characteristics can be used. That is, in the method according to the related art in which the imaging conditions are designed in accordance with the minimum slew rate, since an expensive gradient magnetic field amplifier 3a with good output voltage characteristics is used, the imaging conditions need to be improved. In contrast, according to the second embodiment, it is possible to use various kinds of gradient magnetic field amplifiers 3a and also use inexpensive gradient magnetic field amplifiers 3a.

According to the second embodiment, it is possible to optimize the characteristics of the gradient magnetic field amplifier 3a. That is, the method according to the second embodiment receives the output voltage characteristics of the actually used gradient magnetic field amplifier 3a by real-time feedback and specifies the waveform of the gradient magnetic field pulse that is most suitable for the output voltage characteristics. Therefore, even when there is a variation in the output voltage characteristics of the gradient magnetic field amplifier 3a due to, for example, an individual difference or over time, it is possible to perform the pulse sequence with the waveform of the optimal gradient magnetic field pulse. In addition, it is possible to stabilize the quality of an MR image.

The embodiment is not limited to the above-described embodiments, but various embodiments can be made.

In the first and second embodiments, a single-shot EPI sequence is assumed, but the embodiment is not limited thereto. The embodiment can be similarly applied to a multi-shot EPI sequence requiring a plurality of shots in order to collect the MR echo signals of the entire k-space. In this case, for example, after the one-shot EPI sequence ends, the MRI apparatus 100 waits for the recovery of the output voltage of the gradient magnetic field amplifier 3a and then performs the EPI sequence at the next shot. The embodiment is not limited to the EPI sequence, but can be effectively applied to any pulse sequences that include the application of a continuous read gradient magnetic field pulse and are capable of preventing a reduction in the output voltage of the gradient magnetic field amplifier.

As shown in FIG. 8, the embodiment can be applied to a diffusion weighted image (DWI) sequence using single-shot (SS) spin echo (SE) EPI. FIG. 8 is a diagram illustrating an EPI sequence according to a third embodiment and FIG. 9 is a diagram illustrating a collected MR echo signal.

In the single-shot SE EPI sequence shown in FIG. 8, the collected MR echo signals are arranged around a location in the k-space that is referred to as a 0-phase encode (see FIG. 9) and the time required therefore is referred to as the time of echo "TE."

In the EPI sequence, it is preferable to increase the amount of sampling data in the vicinity of TE. Therefore, when the EPI sequence is performed, the MRI apparatus 100 may reduce the slew rate of the gradient magnetic field pulse before the "0-phase encode" location in k-space (the MRI apparatus 100 may reduce the slew rate). As a result, it is possible to prevent a reduction in the output voltage of the gradient magnetic field amplifier 3a. The MRI apparatus 100 increases the slew rate of the gradient magnetic field pulse in the vicinity of TE and thus increases the amount of valid data. Then, similarly to the first embodiment or the second embodiment, the MRI apparatus 100 may control the gradient magnetic field power supply 3 such that the rising gradient is gradually reduced (i.e., according to a location in k-space of MR echo signal data to be collected).

The following methods are4 used in order to collect the MR echo signal data: a method of inserting "zero" into the k-space locations from which no MR echo signal data is collected, without collecting the MR echo signal data from the line locations of some phase encodes in the k-space (hereinafter, referred to as a zero-filling method); and a method of collecting MR echo signal data for slightly more than one-half (the upper half or the lower half) of the phase-encoded line locations in k-space and estimating the remaining MR echo signal data for other locations in k-space using a mathematical property, such as a Hermitian conjugate (hereinafter, referred to as a half-Fourier method).

The examples shown in FIGS. 8 and 9 correspond to the zero-filling method. The MRI apparatus 100 starts to collect the MR echo signal data from the line of a set of low frequency components and inserts "zero" into the k-space (in FIG. 9, "0 fill").

In the half-Fourier method, the MRI apparatus 100 starts to collect the MR echo signal data from the k-space line location of a set of low frequency components again.

The embodiment can be similarly applied to both a case in which the MR echo signal data is collected by the zero-filling method and a case in which the MR echo signal data is collected by the half-Fourier method.

In each of the collecting methods, for example, control may be performed such that the slew rate of the gradient magnetic field pulse is reduced (control may be performed such that the slew rate is reduced for some locations in k-space) and then the slew rate of the gradient magnetic field pulse increases in the vicinity of TE (i.e., the slew rate is increased for some locations in k-space) to increase the amount of valid data. Then, the gradient magnetic field power supply 3 may be controlled such that the rising gradient of the gradient magnetic field pulse is gradually reduced.

In this case, the MRI apparatus 100 generates pulse sequence execution data for changing the slew rate of the gradient magnetic field pulse. In addition, the MRI apparatus 100 calculates a necessary regridding coefficient or pitch as described in the first embodiment or the second embodiment, and collects the MR echo signal data on the basis of the calculated regridding coefficient or pitch.

As such, in this embodiment, the gradient magnetic field power supply 3 is controlled such that the rising gradient of the gradient magnetic field pulse is gradually reduced, but the embodiment is not limited thereto. The gradient magnetic field power supply 3 may be controlled such that the slew rate of the gradient magnetic field pulse is changed during the pulse sequence.

The multi-shot EPI sequence may be given as an example in which the gradient magnetic field power supply 3 is controlled such that the slew rate of the control gradient magnetic field pulse is changed.

In the multi-shot EPI sequence, the MR echo signal data in the k-space is not necessarily sequentially collected from the high frequency components, but high frequency components and low frequency components may be collected at random.

In this case, the MRI apparatus 100 may appropriately change the slew rate of the gradient magnetic field pulse. For example, when the MR echo signal data for locations of high frequency components in k-space (or low frequency components in k-space) is collected, the MRI apparatus 100 reduces the slew rate of the gradient magnetic field pulse. When the MR echo signal data of locations of low frequency components in k-space (or high frequency components in k-space) is collected, the MRI apparatus 100 increases the slew rate of the gradient magnetic field pulse.

When the slew rate of the gradient magnetic field pulse is reduced, it is possible to prevent a reduction in the output voltage of the gradient magnetic field amplifier 3a. As such, it is possible to effectively use the output voltage of the gradient magnetic field amplifier 3a by appropriately changing the slew rate of the gradient magnetic field pulse.

In this case, the MRI apparatus 100 generates pulse sequence execution data for changing the slew rate of the gradient magnetic field pulse. In addition, the MRI apparatus 100 calculates a necessary regridding coefficient or pitch as described in the first embodiment or the second embodiment and collects the MR echo signal data on the basis of the calculated regridding coefficient or pitch.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
a gantry, static and gradient magnetic field generators, at least one radio frequency (RF) coil coupled to an imaging volume, RF transmitter and RF receiver circuitry coupled to the at least one RF coil, and a gradient magnetic field power supply including a gradient magnetic field amplifier coupled to the gradient magnetic field generators; and
processing circuitry configured to:
A) specify a waveform of a continuous readout gradient magnetic field pulse with a slew rate of the waveform being reduced according to a stepwise reduction in an output voltage of the gradient magnetic field amplifier; and
B) perform an MRI pulse sequence including the application of the continuous readout gradient magnetic field pulse having the specified waveform of step A) with the processing circuitry also controlling the gradient magnetic field power supply.

2. The magnetic resonance imaging apparatus according to claim 1, wherein the processing circuitry is further configured to:
predict, when imaging conditions are received, a stepwise reduction in the output voltage on the basis of the received imaging conditions;
specify the waveform of the gradient magnetic field pulse corresponding to the predicted stepwise reduction;
generate an instruction signal on the basis of the specified waveform of the gradient magnetic field pulse; and
perform the pulse sequence by controlling the gradient magnetic field power supply using the generated instruction signal.

3. The magnetic resonance imaging apparatus according to claim 1, wherein the processing circuitry is further configured to:
measure the output voltage of the gradient magnetic field amplifier;
specify, when the measured output voltage is received, the waveform of the gradient magnetic field pulse corresponding to the measured output voltage;
change an instruction signal that controls the gradient magnetic field power supply on the basis of the specified waveform of the gradient magnetic field pulse; and
perform the pulse sequence by controlling the gradient magnetic field power supply using the changed instruction signal.

4. The magnetic resonance imaging apparatus according to claim 1, wherein the processing circuitry is further configured to:
reduce the slew rate of the waveform of the gradient magnetic field pulse at an interval of one period or an interval of a plurality of periods.

5. The magnetic resonance imaging apparatus according to claim 2, wherein the processing circuitry is further configured to:
reduce the slew rate of the waveform of the gradient magnetic field pulse at an interval of one period or an interval of a plurality of periods.

6. The magnetic resonance imaging apparatus according to claim 3, wherein the processing circuitry is further configured to:
reduce slew rate of the waveform of the gradient magnetic field pulse at an interval of one period or an interval of a plurality of periods.

7. The magnetic resonance imaging apparatus according claim 1, wherein the processing circuitry is further configured to collect a magnetic resonance echo signal using RAMP sampling.

8. The magnetic resonance imaging apparatus according to claim 2, wherein the processing circuitry is configured to collect a magnetic resonance echo signal using RAMP sampling.

9. The magnetic resonance imaging apparatus according to claim 3, wherein the processing circuitry is further configured to collect a magnetic resonance echo signal using RAMP sampling.

10. The magnetic resonance imaging apparatus according to claim 4, wherein the processing circuitry is further configured to collect a magnetic resonance echo signal using RAMP sampling.

11. The magnetic resonance imaging apparatus according to claim 5, wherein the processing circuitry is further configured to collect a magnetic resonance echo signal using RAMP sampling.

12. The magnetic resonance imaging apparatus according to claim 6, wherein the processing circuitry is further configured to collect a magnetic resonance echo signal using RAMP sampling.

13. A magnetic resonance imaging apparatus comprising:
a gantry, static and gradient magnetic field generators, at least one radio frequency (RF) coil coupled to an imaging volume, RF transmitter and RF receiver circuitry coupled to the at least one RF coil, and a gradient magnetic field power supply including a gradient magnetic field amplifier coupled to the gradient magnetic field generators; and processing circuitry configured to:
A) specify a waveform of a continuous readout gradient magnetic field pulse with a slew rate of the waveform being reduced according to a location in k-space of MR echo signal data to be collected; and
B) perform an MRI pulse sequence including the application of the continuous readout gradient magnetic field pulse having the specified waveform of step A) with the processing circuitry also controlling the gradient magnetic field power supply.

14. The magnetic resonance imaging apparatus according to claim 13, wherein the processing circuitry is further configured to change the slew rate of the waveform of the gradient magnetic field pulse at an interval of one period or an interval of a plurality of periods.

15. The magnetic resonance imaging apparatus according to claim 13, wherein the processing circuitry is further configured to collect a magnetic resonance echo signal using RAMP sampling.

\* \* \* \* \*